US010292822B2

(12) United States Patent
Larsen et al.

(10) Patent No.: US 10,292,822 B2
(45) Date of Patent: May 21, 2019

(54) BONE GRAFT CAGE

(71) Applicant: DePuy Synthes Products, Inc., Raynham, MA (US)

(72) Inventors: Scott Larsen, West Chester, PA (US); Ross Hamel, West Chester, PA (US); Glen Pierson, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 15/895,811

(22) Filed: Feb. 13, 2018

(65) Prior Publication Data
US 2018/0168812 A1 Jun. 21, 2018

Related U.S. Application Data

(62) Division of application No. 14/675,313, filed on Mar. 31, 2015, now Pat. No. 9,925,046.

(51) Int. Cl.
*A61F 2/28* (2006.01)
*A61F 2/30* (2006.01)
*A61F 2/46* (2006.01)

(52) U.S. Cl.
CPC ........ *A61F 2/2846* (2013.01); *A61F 2/30907* (2013.01); *A61F 2/4601* (2013.01); (Continued)

(58) Field of Classification Search
CPC .................................................. A61F 2/2846
See application file for complete search history.

(56) References Cited

U.S. PATENT DOCUMENTS 3,710,789 A * 1/1973 Ersek ................. A61B 17/8085
606/281
5,676,697 A 10/1997 McDonald
(Continued)

FOREIGN PATENT DOCUMENTS

CN 103298429 9/2013
EP 0551611 7/1993
(Continued)

OTHER PUBLICATIONS

Gugala et al., "New Approaches in the Treatment of Critical-Size Segmental Defects in Long Bones", Macromol. Symp., No. 253, Wiley-VCH Verlag GmbH & Co. KGaA, Weinheim, 2007, pp. 147-161.

*Primary Examiner* — Bruce E Snow
*Assistant Examiner* — Melissa A Hoban
(74) *Attorney, Agent, or Firm* — Fay Kaplun & Marcin, LLP

(57) ABSTRACT

A device for containing bone graft material includes a mesh outer sleeve extending longitudinally from a proximal end to a distal end and sized and shaped to correspond to a profile of an outer surface of a target bone. The outer sleeve includes a longitudinal slot extending along a length thereof. The device also includes a mesh inner sleeve connected to an interior surface of the outer sleeve via at least one strut so that a bone graft collecting space is defined therebetween. The inner sleeve is sized and shaped to correspond to a profile of a medullary canal of the target bone. In addition, the device includes an interstitial mesh extending radially away from an exterior surface of the inner sleeve toward an interior surface of the outer sleeve to hold graft material in the bone graft collecting space.

11 Claims, 4 Drawing Sheets

(52) U.S. Cl.
CPC .......... *A61F 2002/3024* (2013.01); *A61F 2002/30474* (2013.01); *A61F 2002/30909* (2013.01); *A61F 2002/30911* (2013.01); *A61F 2002/30912* (2013.01); *A61F 2002/30915* (2013.01); *A61F 2002/30948* (2013.01); *A61F 2240/002* (2013.01)

(56) References Cited

U.S. PATENT DOCUMENTS

| | | | |
|---|---|---|---|
| 5,676,699 A * | 10/1997 | Gogolewski | C08L 89/00 623/16.11 |
| 8,092,513 B2 | 1/2012 | Khosravi | |
| 9,925,046 B2 | 3/2018 | Larsen et al. | |
| 2001/0018616 A1 | 8/2001 | Schwab | |
| 2002/0123750 A1 | 9/2002 | Eisermann et al. | |
| 2004/0049270 A1 | 3/2004 | Gewirtz | |
| 2005/0015154 A1 | 1/2005 | Lindsey et al. | |
| 2005/0192675 A1 | 9/2005 | Robinson | |
| 2005/0234557 A1 | 10/2005 | Lambrecht et al. | |
| 2006/0282168 A1 | 12/2006 | Sherman et al. | |
| 2007/0061015 A1 | 3/2007 | Jensen et al. | |
| 2007/0203584 A1 | 8/2007 | Bandyopadhyay | |
| 2008/0269745 A1 | 10/2008 | Justin | |
| 2010/0310623 A1 | 12/2010 | Laurencin et al. | |
| 2011/0054408 A1 | 3/2011 | Wei et al. | |
| 2011/0307073 A1 | 12/2011 | Teoh | |
| 2012/0029102 A1 | 2/2012 | Rose et al. | |
| 2012/0095463 A1 | 4/2012 | Rains et al. | |
| 2012/0296441 A1 | 11/2012 | Mikhail | |
| 2013/0018482 A1 | 1/2013 | Meridew et al. | |
| 2013/0261634 A1 | 10/2013 | McKay | |
| 2014/0364961 A1 | 12/2014 | Mikhail et al. | |

FOREIGN PATENT DOCUMENTS

| | | |
|---|---|---|
| EP | 1 800 627 | 6/2007 |
| KR | 2014/0005174 | 1/2014 |
| WO | 98/38918 | 9/1998 |
| WO | 02/064059 | 8/2002 |
| WO | 2009/025884 | 2/2009 |
| WO | 2010/011941 | 1/2010 |
| WO | 2010/044758 | 4/2010 |
| WO | 2010/093950 | 8/2010 |
| WO | 2011/094748 | 8/2011 |
| WO | 2012/068062 | 5/2012 |
| WO | 2013/006778 | 1/2013 |

* cited by examiner

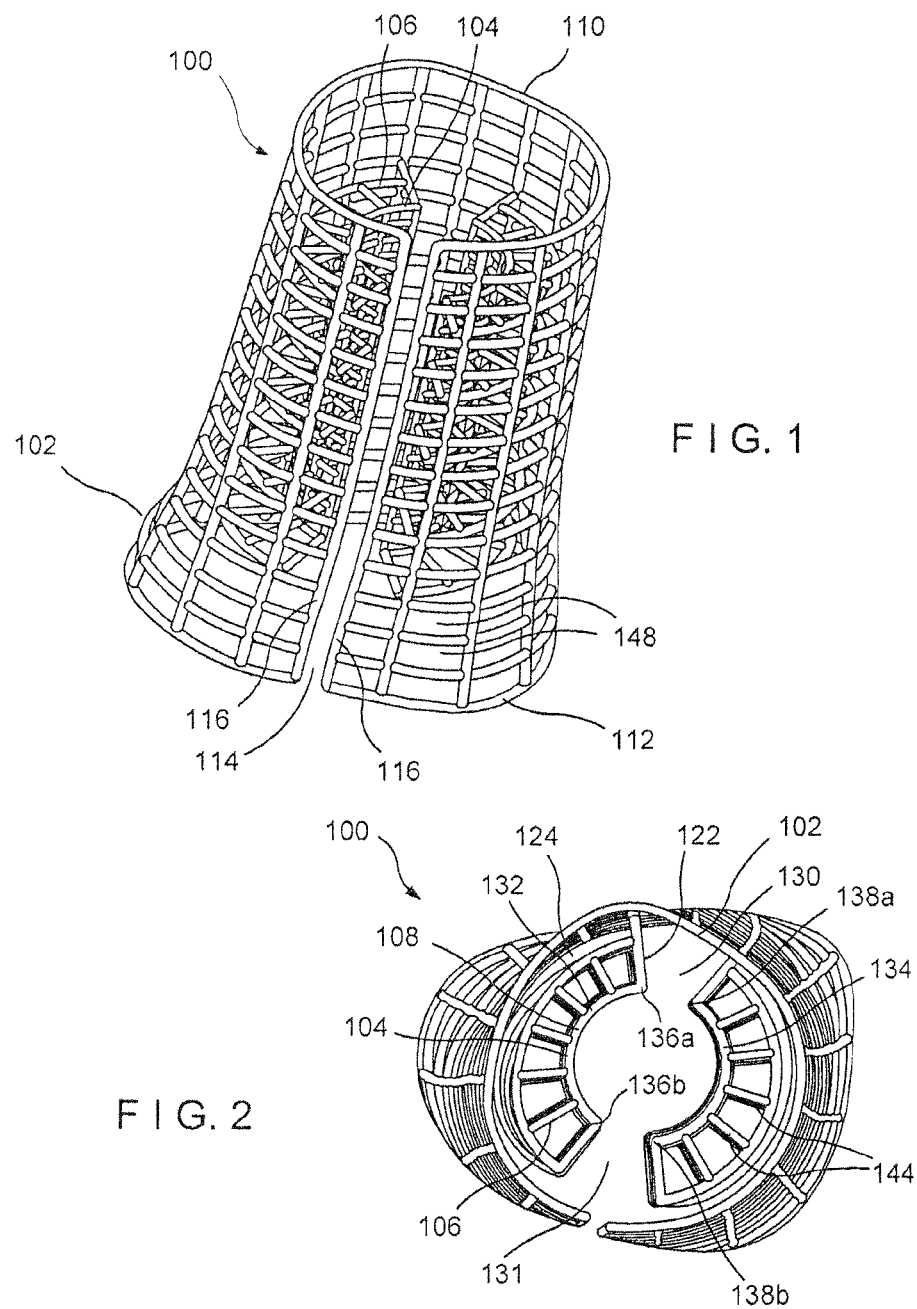

BONE GRAFT CAGE

BACKGROUND

Large bone defects are often treated with implants and/or bone grafts to assist with healing. The bone grafts may be placed in the target area using any of a variety of methods. For example, a graft may simply be placed between two separated ends of an injured or otherwise damaged bone. However, without a container for the bone graft, the graft may fall away from a target site before it can be incorporated by the body into the healing bone. According to another method, PMMA spacers may be placed in the target area so that the fibrous tissue may be formed within the spacers. Subsequently, the PMMA spacers are removed and bone graft material is packed into the capsule formed by the body. Alternatively, some methods have included a mesh placed into the target area to contain the bone graft material at that location. These mesh containers generally include an outer wall with a diameter selected to match an outer surface of the bone to prevent the graft material from falling out of the bone.

SUMMARY OF THE INVENTION

The present invention is directed to a device for containing bone graft material, comprising a mesh outer sleeve extending longitudinally from a proximal end to a distal end and sized and shaped to correspond to a profile of an outer surface of a target bone, the outer sleeve including a longitudinal slot extending along a length thereof along with a mesh inner sleeve connected to an interior surface of the outer sleeve via at least one strut so that a bone graft collecting space is defined therebetween, the inner sleeve sized and shaped to correspond to a profile of a medullary canal of the target bone and an interstitial mesh extending radially away from an exterior surface of the inner sleeve toward an interior surface of the outer sleeve to hold graft material in the bone graft collecting space.

The present invention is also directed to a method for treating a bone with bone graft material, comprising opening a mesh outer sleeve of a bone graft containment device by separating longitudinal edges defining a longitudinal slot extending therealong, packing a bone graft material into an interstitial mesh extending radially away from an exterior surface of a mesh inner sleeve so that the bone graft material is packed against the exterior surface of the inner sleeve, the inner sleeve connected to the outer sleeve via at least one strut so that a bone graft collection space is defined therebetween, positioning the device so that the inner sleeve and interstitial mesh extend in a target area between separated portions of a target bone to be treated and the outer sleeve overlaps ends of the separated portions, and closing the outer sleeve so that the device is mounted over the target bone.

BRIEF DESCRIPTION

FIG. 1 shows a perspective view of a device according to a first exemplary embodiment of the present invention;

FIG. 2 shows a top plan view of the device of FIG. 1;

DETAILED DESCRIPTION

Figure 3:
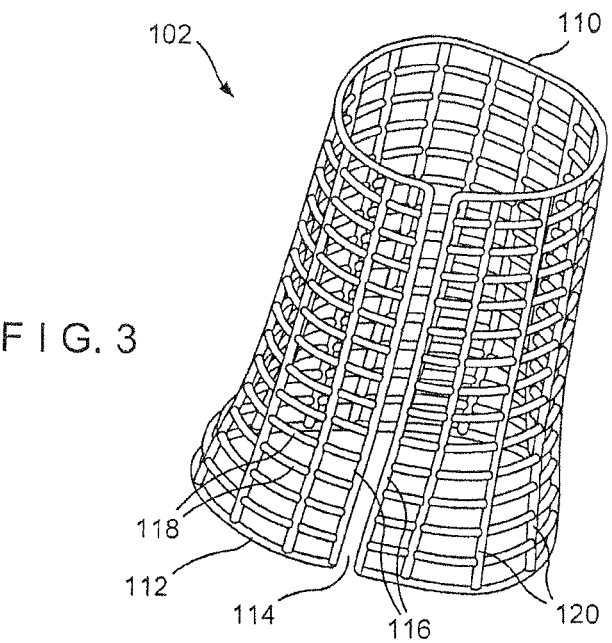
FIG. 3 shows a perspective view of an outer sleeve of the device of FIG. 1.
Figure 4:
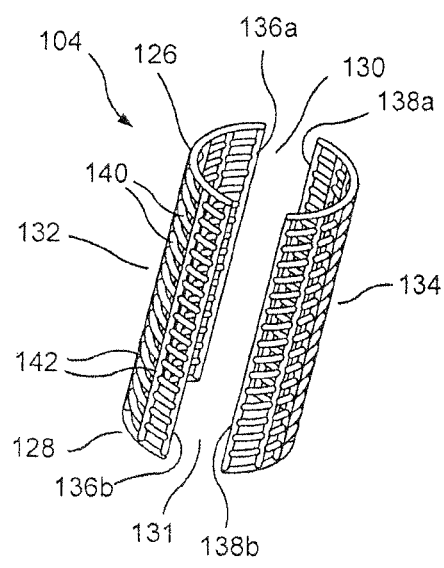
FIG. 4 shows a perspective view of an inner sleeve of the device of FIG. 1.
Figure 5:
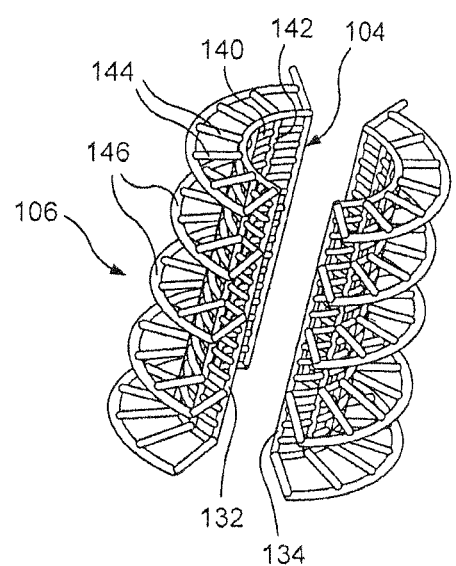
FIG. 5 shows a perspective view of the inner sleeve and an interstitial mesh of the device of FIG. 1.

The present invention may be further understood with reference to the following description and the appended drawings, wherein like elements are referred to with the same reference numerals. The present invention relates to the treatment of bone defects and, in particular, relates to treatments using bone grafts. Exemplary embodiments of the present invention describe a graft containment device configured to be positioned between separated longitudinal portions of a bone such that graft material may be packed therein so that healing may progress through the graft material to join the separated portions of bone. The graft containment device of the exemplary embodiment comprises an interstitial mesh between inner and outer sleeves thereof, the interstitial mesh and the inner sleeve holding the graft material therein and preventing migration of the device along the bone. The device of the present invention may be used to treat non-articular portions of long bone such as, for example, the femur, tibia and humerus.

As shown in FIGS. 1-5, a graft containment device 100 according to an exemplary embodiment of the present invention comprises an outer sleeve 102 and an inner sleeve 104 connected to one another so that, when the device 100 is positioned in a target area between separated longitudinal portions of a target bone, the outer sleeve 102 substantially matches a profile of the outer surface of each of the separated portions of bone while the inner sleeve 104 substantially matches a profile of a medullary canal of the target bone and/or a shape of ends of the separated portions of the target bone. The device 100 also comprises an interstitial mesh 106 extending radially outward from an exterior surface 108 of the inner sleeve 104. The interstitial mesh 106 and the inner sleeve 104 hold graft material packed therein between the outer and inner sleeves 102, 104 and prevents migration of the device 100 along the length of the bone once the device 100 has been positioned in the target area between the separated portions of bone. The outer sleeve 102, inner sleeve 104 and the interstitial mesh 106 of the device 100 are formed via a strut framework so that the device 100 may be three dimensionally built and printed using a patient's specific bone dimensions, which may be obtained, for example, via 3D imaging of the target bone. In particular, circumferential and/or axial driver curves, along with a desired spacing between adjacent struts, may be used as input data for building and printing the device 100.

The outer sleeve 102 extends longitudinally from a proximal end 110 to a distal end 112 and, in this embodiment, defines a generally cylindrical shape corresponding to the profile of the outer surface of the target bone. The outer sleeve 102 further includes a longitudinal slot 114 extending along an entire length thereof so that the outer sleeve 102 may be opened to be positioned about the target bone. In other words, the longitudinal edges 116 defining the longitudinal slot 114 may be separated from one another by spreading the halves of the device 100 apart. As will be understood by those skilled in the art, as the proximal and distal ends 110, 112, respectively, of the outer sleeve 102 are separated by a distance selected to be slightly larger than a distance by which the portions of bone are separated. This allows the outer sleeve 102 to over lap each of the separated portions of bone and to be coupled thereto. Thus, to properly insert the device 100 into the space between the portions of bone, the device 100 needs to be spread open so that these overlapping portions at the proximal and distal ends 110, 112, are on opposite sides of the bone. Then the interstitial mesh 106 and the inner sleeve 104 can be slid into the space between the portions of bone as the outer sleeve 102 is wrapped around the ends of the portions of bone, spanning the space therebetween. As described above, the outer sleeve 102 is built via a strut framework so that the outer sleeve 102 is formed in a mesh configuration. The mesh configuration of the outer sleeve 102 may be formed, for example, via circumferential struts 118 and axial struts 120 intersecting one another. Adjacent circumferential struts 118 and adjacent axial struts 120 may be separated from one another by a distance of between 1.0 mm to 10.0 mm. A length of the outer sleeve 102 is selected so that proximal and distal ends 110, 112 of the outer sleeve 102 overlap portions of the target bone.

The inner sleeve 104 is connected to the outer sleeve 102 via at least one strut 122 so that the inner and outer sleeves 104, 102 are separated from one another via a substantially annular space 124. The inner sleeve 104 extends longitudinally from a proximal end 126 to a distal end 128 and defines a shape substantially corresponding to a medullary canal of the target bone and has a length substantially corresponding to the distance of separation between the portions of bone (i.e., slightly shorter than the outer sleeve 102). Where the inner sleeve 104 is connected to the outer sleeve 102 via a plurality of struts 122, the inner sleeve 104 includes a pair of diametrically opposed longitudinal slots 130, 131 extending along an entire length thereof so that the inner sleeve 104 is separated into a first clamshell portion 132 and a second clamshell portion 134 in which longitudinal edges 136a, 136b of the first clamshell portion 132 are separated from longitudinal edges 138a, 138b of the second clamshell portion 134. The inner sleeve 104 may be connected to the outer sleeve 102 via struts 122 along longitudinal edges 136a, 138a defining one of the longitudinal slots 130 so that the inner sleeve 104 may be opened to be positioned in the target area via the second one of the longitudinal slots 131. The connection of the inner sleeve 104 to the outer sleeve 102 along the first longitudinal slot 130 forms a living hinge along a length of the outer sleeve 102 along which the inner sleeve 104 is connected, so that the device 100 may be opened, as desired. In other words, similarly to the outer sleeve 102, longitudinal edges 136b, 138b defining the second longitudinal slot 131 may be separated from one another to position the device 100 in the target area and to fill the device 100 with graft material. Specifically, the halves of the outer sleeve 102 may be separated to expose the inner sleeve 104 so that the graft material may be packed thereagainst. Once the graft material has been packed therein, the first and second clamshell portions 132, 134 may be separated to position the inner sleeve 104 about an intramedullary nail implanted within the target hone, while the halves of the outer sleeve 102 are positioned about the separated ends of the target hone. Connecting the inner sleeve 104 along only one of the longitudinal slots 130 permits the inner sleeve 104 to "float" within the outer sleeve 102. Thus, if the device 100 is being utilized with a target bone having an intramedullary nail implanted therein, as described above, the inner sleeve 104 is movable relative to the outer sleeve 102 to find the intramedullary nail for cases in which the intramedullary nail is not centered within the target bone.

Figure 6:
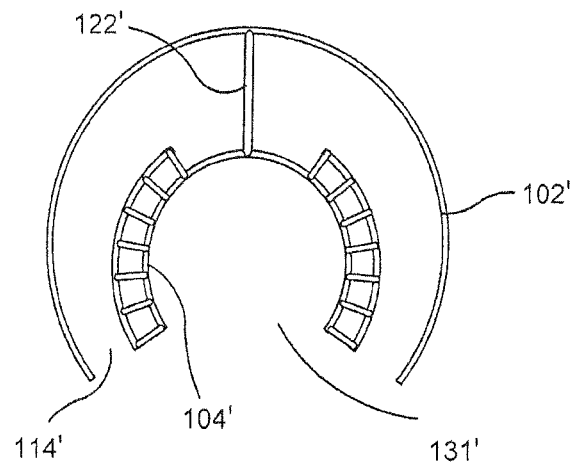
FIG. 6 shows a top plan view of a device according to another embodiment of the present invention.

In another embodiment, as shown in FIG. 6, an inner sleeve 104' may be substantially similar to the inner sleeve 104 except that the inner sleeve 104' is connected to an outer sleeve 102' via a single strut 122'. Where the inner sleeve 104' is connected to the outer sleeve 102' via a single strut 122', the inner sleeve 104' may include a single longitudinal slot 131' extending along an entire length thereof. The single strut 122' may extend from a portion of an exterior surface of the inner sleeve 104' substantially opposing the longitudinal slot 131' to connect to the interior surface of the outer sleeve 102' such that the longitudinal slot 114 of the outer sleeve 102' and the longitudinal slot 131' of the inner sleeve 104' are substantially aligned. Thus, similarly to the inner sleeve 104 connected to the outer sleeve 102 via a plurality of struts 122, halves of the inner and outer sleeves 104', 102' may be opened to position the inner and outer sleeves 104', 102 about the intramedullary nail and separated ends of the target bone, respectively.

A length of the inner sleeve 104 may be selected so that the inner sleeve 104 may be positioned between the separated portions of the target bone without contacting ends of the separated portions of bone. For example, the proximal and distal ends 126, 128 of the inner sleeve 104 may be separated from the ends of the separated portions of the bone by at least 2.0 mm to prevent interference with the bone. Similarly to the outer sleeve 102, the inner sleeve 104 may be formed of circumferential and axial struts 140, 142 intersecting one another. A distance between adjacent circumferential and axial struts may range from between 1.0 mm and 10.0 mm. It may be desired, however, for the inner sleeve 104 to have a smaller mesh (i.e., smaller distance between adjacent struts) so that graft material that is packed thereagainst is prevented from passing therethrough.

The interstitial mesh 106 is connected to the outer surface 108 of the inner sleeve 104 (i.e., the surface of the inner sleeve 104 facing the outer sleeve 102) and is comprised of a plurality of struts 144 extending radially outward from the outer surface 108. The struts 144 in this embodiment are substantially perpendicular to the struts 140, 142 of the inner sleeve 104. The interstitial mesh 106 may also include circumferential struts 146 connecting radially outermost ends of adjacent struts 144. An exterior surface 148 of the interstitial mesh is separated from an interior surface 150 of the outer sleeve 102. Upon opening of the device 100, graft material may be packed into the interstitial mesh 106 against the inner sleeve 104. The interstitial mesh 106 acts to hold the graft material within the device 100 and prevent axial migration of the graft material out of the target area.

Since the device 100 may be custom built and printed for a specific patient, the length, circumference and shape of the outer sleeve 102 may be customized. For example, the length of the outer sleeve 102 may be selected so that, when the outer sleeve 102 is positioned in the target area about the target bone, proximal and distal ends 110, 112 of the outer sleeve 102 overlap the bone by, for example, at least 5 mm on each side. The length of the inner sleeve 104 may be selected so that there is a clearance between the end surfaces of the portions of bone and the ends of the inner sleeve of at least 2 mm at the proximal and distal ends 126, 128 of the inner sleeve 104. In one embodiment, lengths of the outer and inner sleeves 102, 104 may be adjusted in increments of 5 mm. It will be understood by those of skill in the art, however, that dimensions of the device 100 may be varied, as desired and suited for a specific patient. The device 100 may be formed of biodegradable polymers such as, for example, polycaprolactone (PCL), which is both printable and bioresorbable.

According to an exemplary method, the device 100 may be custom-built and printed to suit a specific patient's bone dimensions and needs. In particular, a target bone of a patient may be imaged to obtain bone dimensions such as, for example, circumferences of both an outer surface and an inner surface (i.e., corresponding to a medullary canal) of a desired portion of the target bone, along with a length of a portion of the bone to be treated (i.e., a distance between separated portions of the target bone). These dimensions may be used to enter input data to build and print the device 100 using, for example, CAD software. Once the device 100 has been built, as described above, the device 100 may be positioned in the target area between separated portions of the target bone.

In particular, the outer sleeve 102 may be opened by separating longitudinal edges 116 thereof. Graft material may then be packed into the interstitial mesh 106 against the inner sleeve 104. As described above, the mesh of the inner sleeve 104 is configured to prevent the graft material packed thereagainst from passing therethrough and leaving the target area. Once the graft material has been packed into the interstitial mesh 106, the device 100 may be positioned in the target area. For cases in which the device 100 is being utilized with a target bone having an intramedullary nail positioned therein, the inner sleeve 104 may also be opened by separating longitudinal edges 136*b*, 1368*b* so that the inner sleeve 104 may be positioned about the intramedullary nail while the outer sleeve 102 is positioned about the target bone. In particular, the inner sleeve 104 is positioned between ends of the separated portions of the bone so that proximal and distal ends 126, 128 of the inner sleeve 104 extend entirely between the separated portions of the bone. Proximal and distal ends 110, 112 of the outer sleeve 102, however, should overlap portions of the target bone. In one example, the proximal end and distal ends 110, 112 may each overlap ends of the separated portions of bone by at least 5 mm.

Graft material may also be inserted at the ends of the device 100, between the proximal and distal ends 126, 128 of the inner sleeve 104 and the ends of the separated portions of bone. Once the device 100 has been positioned, as desired, the outer sleeve 102 may be closed by drawing the longitudinal edges 116 toward one another. The longitudinal edges 116 may be sutured together to fix the device 100 over the target bone. Additional graft material may be packed into device via the mesh of the outer sleeve 102 upon positioning the device 100 over the bone, as described above.

The overlapping of the proximal and distal ends 110, 112 over ends of the separated portions of bone and the positioning of the inner sleeve 104 between two portions of bone is sufficient to hold the device 100 in position over the target area of the bone. In particular, the interstitial mesh 106 and the inner sleeve 104 help to prevent migration of the device 100 along the bone. In some cases where additional fixation is desired, however, a user (e.g., surgeon) may insert a bone fixation element through an opening 148 formed in the mesh pattern of the outer sleeve 102 and into the bone. For example, a bone screw may be inserted into an opening of the mesh structure at each of the proximal and distal ends 110, 112 into the bone.

In some cases, the user may desire to further customize the device 100 during the grafting process. In these cases, the user may cut portions of the device 100 to accommodate the specific needs of the patient's bone. The device 100 may be formed of a material that may be cut using, for example, a scissor or other cutting tool. For example, if desired, the user may adjust a length of the outer sleeve 102 to suit a patient's specific needs and/or to create less overlap between the device 100 and the bone.

Although the exemplary method is describes the device 100 as being utilized with a target bone having an intramedullary nail implanted therein, it will be understood by those of skill in the art that the intramedullary nail is not a requirement of the device 100. The device 100 may also be utilized with other bone fixation implants such as, for example, a bone plate. Where the device 100 is being used with a bone plate rather than an intramedullary nail, the inner sleeve 104 may simply be fixed in a closed configuration via, for example, suturing, prior to closing the outer sleeve 102 about the target bone. Alternatively, although the inner sleeve 104 is shown and described as forming two clamshell portions, the inner sleeve 104 may be substantially cylindrical so that fixing the inner sleeve 104 in the closed configuration is not required.

Figure 7:
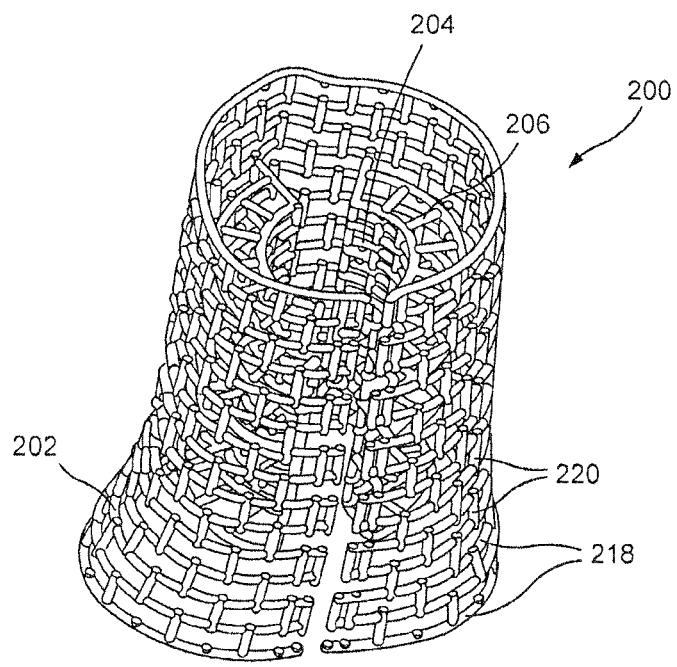
FIG. 7 shows a perspective view of a device according to another exemplary embodiment of the present invention.

Although the outer and inner sleeves 102, 104 of the device 100 is shown and described as being formed of circumferential and axial struts that intersect one another, it will be understood by those of skill in the art that the outer and inner sleeves 102, 104 may be formed of any of a variety of mesh structures and patterns so long as the device 100 is formed via a strut framework. For example, as shown in FIG. 7, a device 200 may be substantially similar to the device 100 comprising an outer sleeve 202, an inner sleeve 204 and an interstitial mesh 206. Rather than circumferential and axial struts that intersect one another to form a substantially grid-like pattern as shown and described with respect to device 100, however, the outer sleeve 202 may be formed of circumferential struts 218 connected to one another via axial struts 220 alternatingly interrupted along a length thereof to form the interrupted square mesh pattern shown in FIG. 7. In particular, the axial struts 220 are interrupted between adjacent circumferential struts 218 so that openings defined by the intersecting struts appear to be offset from one another. Although not shown, the mesh of the inner sleeve 204 may be similarly constructed to the outer sleeve 202, including circumferential struts connected to one another via alternatingly interrupted axial struts.

Figure 8:
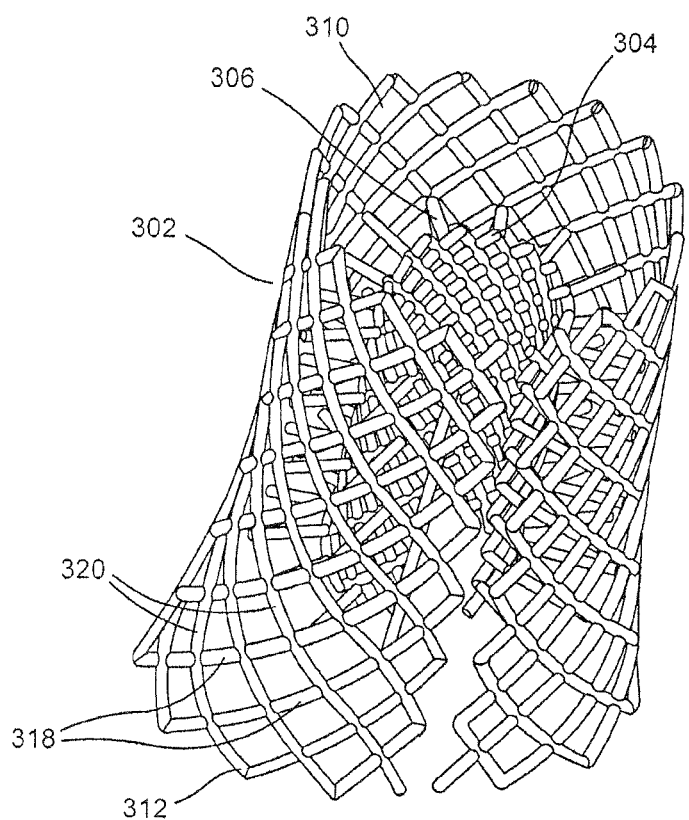
FIG. 8 shows a perspective view of a device according to yet another exemplary embodiment of the present invention.
Figure 9:
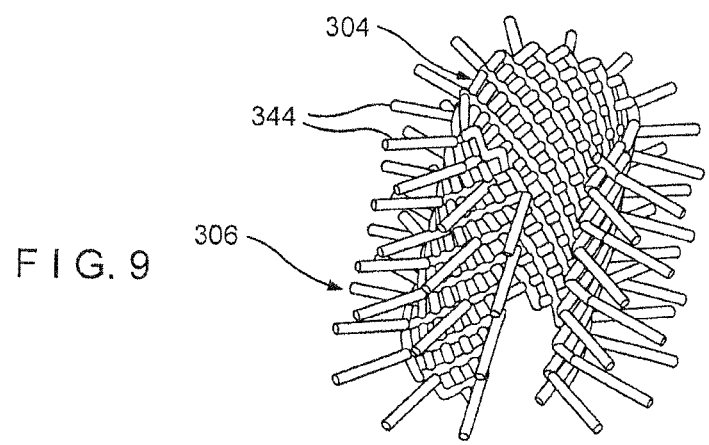
FIG. 9 shows an inner sleeve and an interstitial mesh of the device of FIG. 8.

In another embodiment, as shown in FIGS. 8-9, a device 300 may be substantially similar to the devices 100, 200 described above, comprising an outer sleeve 302, an inner sleeve 304 and an interstitial mesh 306. Rather than the grid-like mesh or the interrupted mesh patterns shown and described in regard to the devices 100, 200, respectively, the outer and/or inner sleeves 302, 304 may have a diamond mesh pattern. In particular, rather than circumferential and axial struts, the outer sleeve 302, for example, includes a plurality of first struts 318 extending in a clockwise direction from a proximal end 310 of outer sleeve 302 to a distal end 312 of the outer sleeve 302 and a plurality of second struts 320 extending in a counter-clockwise directing from the proximal end 310 to the distal end 312 such that the first and second struts intersect one another to form a diamond mesh pattern. The inner sleeve 304 may be constructed in a similar manner to form a diamond mesh pattern.

The interstitial mesh 306 may be substantially similar to the interstitial mesh 106, including a plurality of struts 344 extending radially outward from an exterior surface 308 of the inner sleeve 304. The device 300 does not show circumferential struts connecting radially extending ends of adjacent struts 344. It will be understood by those of skill in the art, however, that these circumferential struts may be included. In another embodiment, rather than circumferential struts, the device 300 may include a diagonally extending strut connecting radially extending ends of adjacent struts 344.

Different mesh patterns may be chosen in addition to those described here. Mesh patterns may be chosen to create a particular level of flexibility of the device 300. Mesh patterns may also be chosen to prevent buckling of the device 300.

It will be understood by those of skill in the art that various modification and variations may be made in the structure and methodology of the present invention, without departing from the spirit or the scope of the invention. Thus, it is intended that the present invention cover the modifications and variations of this invention provided that they come within the scope of the appended claims and their equivalents.

What is claimed is:

1. A method for treating a bone with bone graft material, comprising:
    opening a mesh outer sleeve of a bone graft containment device by separating longitudinal edges defining a longitudinal slot extending therealong;
    packing a bone graft material into an interstitial mesh extending radially away from an exterior surface of a mesh inner sleeve toward the interior surface of the outer sleeve so that the bone graft material is packed against the exterior surface of the inner sleeve, an exterior surface of the interstitial mesh separated from an interior surface of the mesh outer sleeve so that, when the longitudinal edges are separated, the outer sleeve is moved away from the interstitial mesh, the inner sleeve connected to the outer sleeve via at least one strut so that a bone graft collection space is defined therebetween;
    positioning the device so that the inner sleeve and interstitial mesh extend in a target area between separated portions of a target bone to be treated and the outer sleeve overlaps ends of the separated portions; and
    closing the outer sleeve so that the device is mounted over the target bone.

2. The method of claim 1, further comprising suturing longitudinal edges of the longitudinal slot of the outer sleeve together to hold the outer sleeve closed.

3. The method of claim 1, wherein the inner sleeve includes a first longitudinal slot extending along an entire length thereof, the inner sleeve connected to the interior surface of the outer sleeve via one strut extending from a portion of the exterior surface of the inner sleeve substantially opposing the first longitudinal slot.

4. The method of claim 3, wherein the inner sleeve including a second longitudinal slot diametrically opposing the first longitudinal slot to define a first clamshell portion and a second clamshell portion, the first and second clamshell portions connected to the interior surface of the outer sleeve via a plurality of struts extending along longitudinal edges of the first and second clamshell portions defining the second longitudinal slot.

5. The method of claim 3, wherein positioning the inner sleeve and the interstitial mesh in the target area includes opening the inner sleeve by separating longitudinal edges defining the first longitudinal slot to position the inner sleeve about an intramedullary nail extending through a medullary canal of the target bone.

6. The method of claim 1, further comprising building and printing the device using dimensions of the target bone.

7. The method of claim 6, further comprising selecting a length of the outer sleeve so that proximal and distal ends thereof overlap ends of separated portions of the target bone, when positioned in the target area.

8. The method of claim 6, further comprising selecting a length of the inner sleeve so that proximal and distal ends thereof are offset from ends of the separated portions of the bone.

9. The method of claim 1, further comprising cutting a portion of the outer sleeve to adjust a length thereof.

10. The method of claim 1, wherein one of the inner and outer sleeves is forming of a plurality of circumferential struts and a plurality of axial struts intersecting one another.

11. The method of claim 1, wherein one of the inner and outer sleeves is formed of a plurality of first struts extending in a clockwise direction from a proximal end to a distal end and a plurality of second struts extending in a counter clockwise direction from a proximal end to a distal end such that the first and second struts intersect one another to form a diamond mesh pattern.

* * * * *

UNITED STATES PATENT AND TRADEMARK OFFICE
CERTIFICATE OF CORRECTION

PATENT NO. : 10,292,822 B2  
APPLICATION NO. : 15/895811  
DATED : May 21, 2019  
INVENTOR(S) : Larsen et al.

Page 1 of 1

It is certified that error appears in the above-identified patent and that said Letters Patent is hereby corrected as shown below:

In the Claims

Column 8, Claim 10, Line 34:
"outer sleeves is forming of a plurality of circumferential" should read "outer sleeves is formed of a plurality of circumferential".

Signed and Sealed this
Twenty-third Day of July, 2019

Andrei Iancu
*Director of the United States Patent and Trademark Office*